United States Patent [19]

Flynn, Jr. et al.

[11] Patent Number: 5,403,093
[45] Date of Patent: Apr. 4, 1995

[54] DT/DT DETECTOR FOR CELL PACK CHARGE DETERMINATION

[75] Inventors: William E. Flynn, Jr., Naugatuck; Joseph G. Murtha, Monroe, both of Conn.

[73] Assignee: Anton/Bauer, Inc., Shelton, Conn.

[21] Appl. No.: 152,432

[22] Filed: Nov. 12, 1993

[51] Int. Cl.⁶ ................... G01N 25/00; G08B 21/00; G01R 31/36
[52] U.S. Cl. ..................... 374/45; 364/481; 324/427; 320/48; 374/102; 340/636
[58] Field of Search ............ 374/45, 102; 320/35, 320/48; 324/105, 427, 431; 364/481, 557; 340/636

[56] References Cited

U.S. PATENT DOCUMENTS

| | | | |
|---|---|---|---|
| 4,377,787 | 3/1983 | Kikuoka et al. | 320/427 |
| 4,755,735 | 7/1988 | Inakagata | 320/35 |
| 4,965,738 | 10/1990 | Bauer et al. | 320/48 |
| 5,047,961 | 9/1991 | Simonsen | 320/48 |
| 5,162,741 | 11/1992 | Bates | 324/427 |
| 5,252,906 | 10/1993 | Busson | 320/35 |
| 5,321,626 | 6/1994 | Palladino | 340/636 |
| 5,321,627 | 6/1994 | Reher | 324/427 |
| 5,345,392 | 9/1994 | Mito et al. | 340/636 |
| 5,349,535 | 9/1994 | Gupta | 320/48 |

*Primary Examiner*—Diego F. F. Gutierrez
*Attorney, Agent, or Firm*—Kramer, Brufsky & Cifelli

[57] ABSTRACT

A technique for detecting when a full charge for a cell pack is reached based upon sensing an actual temperature of the cell pack. The initial actual temperature is the first value stored as a reference temperature. During subsequent sampling events, the actual temperature is stored as the reference temperature when the actual temperature exceeds said reference temperature. A first value for each sample event is stored in a rollover memory when said actual temperature exceeds the reference temperature, and a second value is stored in the rollover memory when the actual temperature does not exceed the reference temperature. The occurrences of the first values is summed for a series of consecutive sampling events to derive a total. The total is compared to a predetermined limit, and if the total is greater, then charging of the cell pack will be discontinued.

4 Claims, 3 Drawing Sheets

DT/DT DETECTOR FOR CELL PACK CHARGE DETERMINATION

FIELD OF THE INVENTION

The present invention relates to a detector for determining the charge on a cell pack (electrical cell or battery) and, more specifically, to an application of the known dT/dt method in a manner such that less RAM computer storage space is required than with traditional dT/dt methods.

SUMMARY OF THE INVENTION

One embodiment of the present invention comprises a technique for detecting the actual temperatures of an object as a function of time. The initial value of actual temperature is stored as a reference temperature. During subsequent sampling events, the reference temperature is incremented when the actual temperature exceeds said reference temperature. A first value for each sample event is stored in a rollover memory when said actual temperature exceeds the reference temperature, and a second value is stored in the rollover memory when the actual temperature does not exceed the reference temperature. The occurrences of the first values is summed for a series of consecutive sampling events to derive a total.

BACKGROUND OF THE INVENTION

The present method is typically utilized with a cell pack that is being charged by a cell pack charger (in this disclosure, the term "cell pack" is intended to cover batteries, cells, or any similar device which chemically stores an electrical charge), and can detect when the cell pack has reached its fully charged state. A characteristics of many cell packs is that the temperature of the cell pack will remain at a nearly constant level when it is being charged in a discharged state. If the charger is still applying charge to the cell pack in a fully charged state, then the temperature of the cell pack will continue to increase, giving off the energy of the charging electrons in the form of heat. This heat can eventually lead to damage or destruction of the cell pack.

It is recognized in the cell pack art that monitoring the temperature change with respect to time (dT/dt, where T represents the temperature of the cell pack, and t represents the time) provides an accurate method of determining the charge level of the cell pack. Previously, computers have been applied to automate the dT/dt detection. However, in those cases where the sample period (time between successive sampling events) is very small, and/or the time over which the computer is storing dT/dt samples is long, then a large amount of computer storage space (RAM memory) will be required. Since it may be desirable to use a computer which has a small memory, or a larger computer in which much of the memory is being utilized for other purposes, then the prior methods may prove ineffective.

It is evident from the above paragraphs that a method for detecting the charge state of a battery using the dT/dt detector which requires only a relatively small amount of computer memory would be useful and desirable.

DETAILED DESCRIPTION OF THE INVENTION

Figure 1:
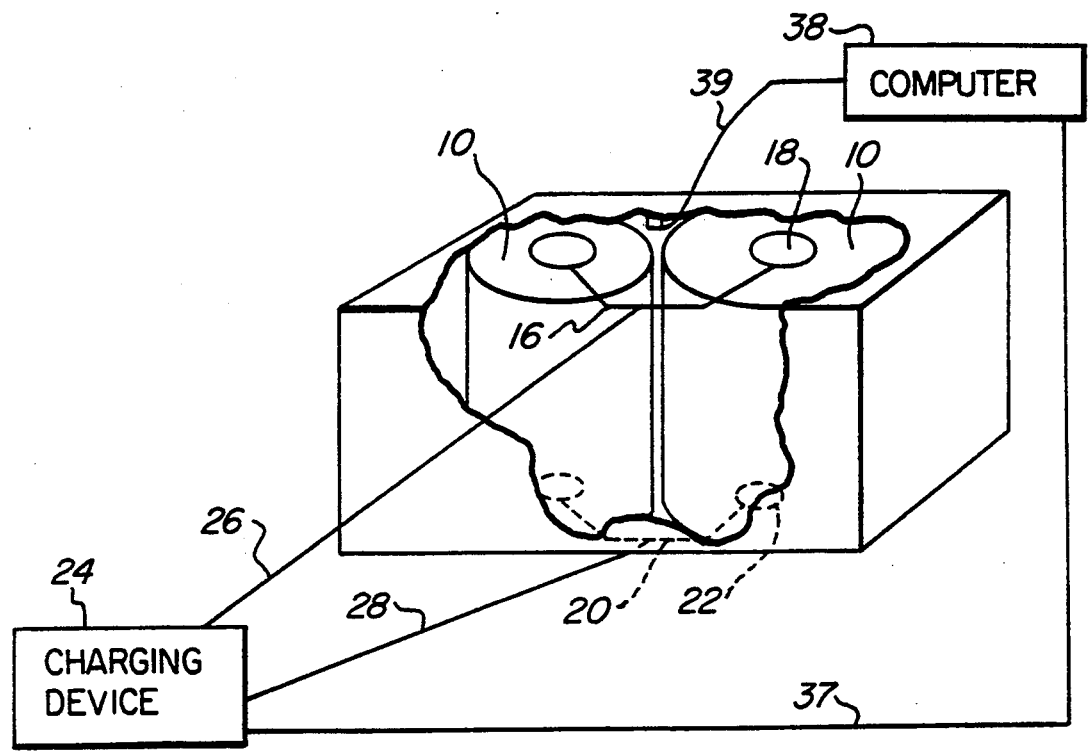
FIG. 1 illustrates a typical prior art configuration for charging a cell pack.

In this disclosure, like elements in the different embodiments will be provided with like reference characters. The specific embodiments, chemicals, values and percentages demonstrated are for illustrative purposes only, and are not intended to be limiting in scope.

A typical cell pack charging configuration of the prior art is illustrated in FIG. 1. One or a plurality of cells 10 are contained in each cell pack 12. Any plurality of cells 10 is also defined as a battery. For this purpose, the term "cell pack" shall be interpreted to include single cells 10 as well as batteries. Each cell pack 12 typically includes a casing 14 (with the cover partially broken away for demonstration purposes) which includes a connector 16 which is connected to all positive electrodes 18, and a connector 20 for all negative electrodes 22. A charging device 24 applies an electrical charge to the electrodes 18, 22 of the cell pack 12 in a known manner using leads 26 and 28 which are in communication with connectors 16, 20, respectively. There is a temperature transducer 34 which is connected to a computer 38 by electrical conduit 39. A portion of the computer 38 stores the cell pack temperature (utilizing transducer 34) for each sampling event. The interval between successive sampling events is determined by the type and size of the cell pack 12. For example, a suitable sampling period (time between sampling events) for a large battery will typically be longer than for a smaller battery of the same type. The manufacturer of each type and size of cell pack usually has the applicable charging information as to cell pack sampling period and voltages ranges. There is a disconnect cable 37 which, when a signal is transmitted therethrough, will cause the charging device 24 to discontinue charging of the cell pack 12.

Figure 2:
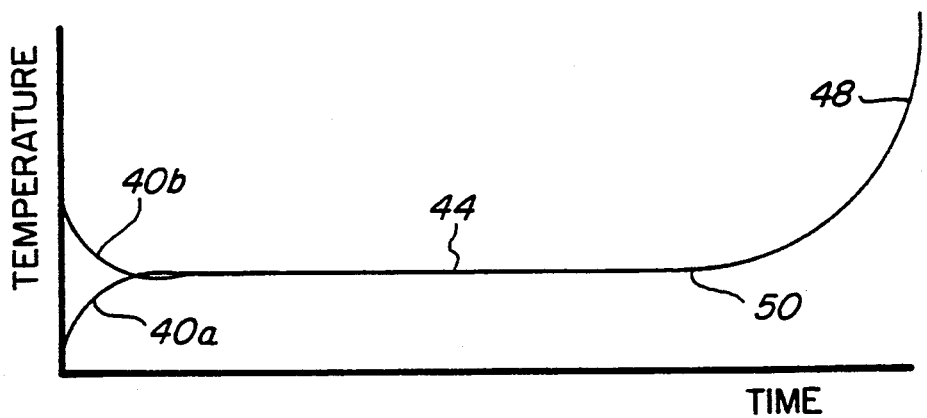
FIG. 2 illustrates a typical temperature vs. time (dT/dt) graph of certain types of cell packs, in which the cell pack is undergoing a charging process.

FIG. 2 illustrates a typical charging graph of the cell pack 12 as a function of time. The temperature and time scales are arbitrary and differ from cell pack to cell pack, but have been found typical of nickel cadmium (NiCd) and nickel metal hydride (NiMH) batteries. It is believed that there are other batteries which demonstrate similar temperature vs. time plots under charging conditions. There are two potential plots 40a and 40b that could occur during the initial stages of charging cell pack 12. Plot 40a is called the incrementing initial period while FIG. 40b is called the decrementing initial period. There are several technical reasons that determine whether the initial period of the FIG. 2 plot will be of an incrementing or decrementing type, as illustrated in 40a and 40b, respectively. These reasons are well known to those skilled in the art, and will not be discussed in further detail here.

After one of the initial charging periods 40a or 40b is completed, the temperature of the cell pack 12 will remain at a relatively constant level for a period of time known as the charging period 44. During the charging period 44, the cell pack 12 is converting virtually all of the electrical charge that is being applied into stored energy. After the charging portion 44 is complete, the cell pack 12 will enter the post charge period 48 which represents that period where almost all of the electrons applied by the charging device to the cell pack 12 are being converted into heat (since the cell pack is fully charged at this portion). The converted heat will usually accumulate and raise the temperature of the cell pack 12 very rapidly, until serious damage or destruction occurs to the cell pack. It is therefore desirable to stop applying any charge to the cell pack 12 after the FIG. 2 plot reaches a junction 50 of the charging period 44 and the post period 48.

One technique used to determine when junction 50 has occurred is the dT/dt method (where T represents temperature, t represents time, and d represents the differential operator). In the dT/dt method, the computer 38 stores the temperature of each successive sampling event. The computer then determines the incremental rise in temperature rise for a series of successive sampling periods for each sampling event. In FIG. 2, for example, the prior art dT/dt method will compute the sum of incremental temperature increases of the cell pack over a specified number of consecutive sampling periods, divided by the total elapsed time. This process is repeated for each new sampling event. Each of the values received for each sampling event is then stored. The slope of the post charging period 48 is assumed by the prior art dT/dt method to be greater than the slope of the incrementing initial portion 40a, or it is assumed that the dT/dt method commences after the incrementing initial period 40a.

An illustrative example of the prior art dT/dt method assumes that the user is interested in terminating charge when a 6 degree rise occurs over a 15 minute period and sampling events occur at 10 second intervals (this requires a total of 6 sampling events/minute times 15 minutes=90 bytes of computer RAM is required). Each 10 seconds, the newest sample is compared to the oldest sample, and if the difference is 6 (in this example) or greater, then the computer 38 will send a signal (over the disconnecting cable 37) to the charging device 24 causing it to cease operation. Compare these 90 bytes of RAM to approximately 256 bytes of memory which typically exist in certain microprocessors, and almost half of the total computer memory (RAM) is used for the dT/dt method using prior art methods.

It becomes evident that much computer memory storage space (RAM) is used in the prior art dT/dt method. This may be acceptable if a large computer with an excess of computer memory space is used. However in those cases where the computer is small (for example a microprocessor or microcomputer) and/or much of the computer storage space is already being used, then the prior art dT/dt method may be restrictive. Also, even if a large computer 38 with an excess of storage space is being used, the prior art dT/dt method may cause the computer to run too slow to effectively turn off the charging device 24 before damage has occurred to the cell pack 12.

HARDWARE OF THE PRESENT EMBODIMENT

Figure 3:
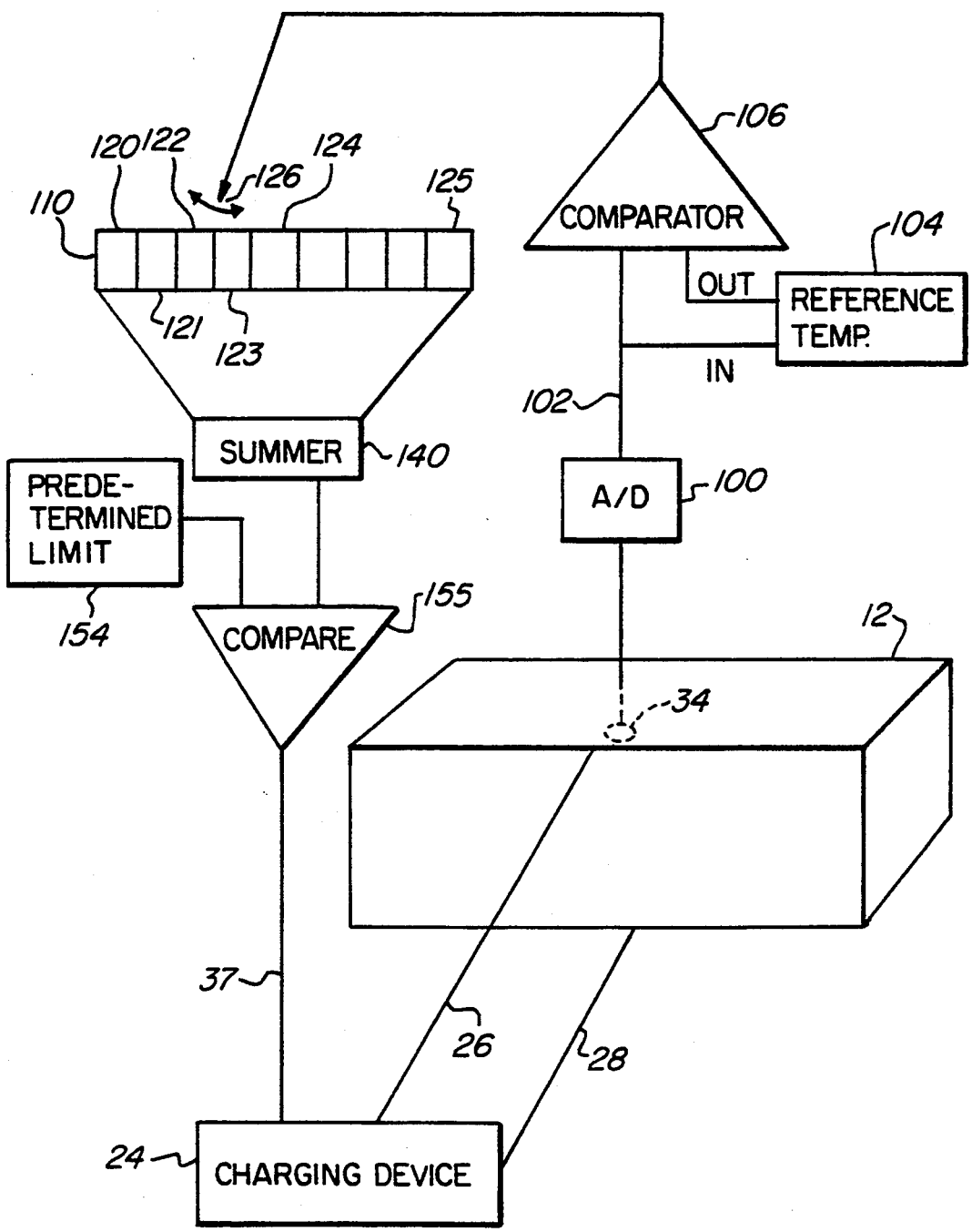
FIG. 3 illustrates one embodiment of the present invention for charging a cell pack of the present invention which is similar to FIG. 1, except for the hardware of the present invention.

The present dT/dt method uses a hardware set-up as illustrated in FIG. 3 in which a present embodiment of the computer 38a is illustrated. The temperature transducer 34 which is encased within the cell pack 12 in a similar manner to that illustrated in FIG. 1 is electrically coupled to an A/D converter 100 which quantizes the temperature value for each sampling event. There are two temperature values which are utilized by the present invention. The first temperature value is the actual temperature value, which is the quantized value from the output 102 of the A/D converter. The second value is contained in a reference temperature store 104, whose operation will be described later. The output values of the reference temperature store 104 and the actual temperature at 102 are fed into a comparator 106. There is a temperature counter 110 which determines the number of times within a specified number of successive sampling events that the actual temperature value exceeds the reference temperature store 104 value.

The present invention determines whether the cell pack 12 has achieved the post charge portion 50 of FIG. 2. First, the FIG. 3 embodiment takes the output 102 of the A/D converter 100 (the actual temperature) and applies it to the reference temperature store 104 for its initial value. At each subsequent sampling event, the value of the actual temperature (output 102) is compared to the value stored in the reference temperature store 104 by comparator 106. Comparator 106 is designed to register a value of 1 if the actual temperature 102 is greater than the reference temperature store 104, or a value of 0 if the actual temperature 102 is less than or equal to the reference temperature store 104.

The sampling period for the present invention is selected such that the maximum temperature change between successive sampling events is 1 degree. If the variation between any successive sampling events is greater than 1 degree, then too long of a sampling period has been selected by the user and it should be decreased. Assuming that the temperature of the cell pack is increasing, then the only two quantized values which are permitted at the output of the comparator 106 are a 1 and a 0.

The above values of 0 or 1 are then input into the temperature counter 110 (which is a roll-over counter). The first input will be input as the left-most bit location 120 while the applicable value of 0 or 1 will be input as successive bit locations 121, 122, 123, . . . , 125. The number of bit locations will be a function of roll over temperature counter 110 design. As soon as all of the bit locations 120–125 contain a value (hereafter referred to as either "0's" or "1's") the latest value of any subsequent sampling event will be input into the right most bit location 125; each previous value for sampling events 121–124 will be incremented to the left by one bit; and the bit formerly in the left bit location 120 will be deleted. A ring pointer 126 points to the particular bit location that is being input by the sampling event, which is typically either the right most bit location 125, or if there are empty bit locations, the left most empty bit location of the temperature counter 110.

Another method to view the process described in the prior paragraph is that the temperature counter 110 contains "0's" or "1's" corresponding to the most recent sampling events. The maximum number of "1's" and "0's" will correspond to the number of bit locations (120–125) that are contained within the temperature counter 110 (providing that there have been that many sampling events taken so far). All the values for sampling events which are older than this have been replaced and discarded.

For each sampling event, the number of "1's" contained in the temperature counter 110 will be summed and the value inserted into a summer 140. The value of the summer 140 will be compared to a predetermined limit device 154 (which is set by the user, and differs between cell packs). When the two values are equal, the user knows that the temperature of the cell pack 12 is increasing at a rate that indicates that the cell pack is within the post charging portion 48 of FIG. 2. At this point, the disconnect cable 37 is actuated, and the charging device 24 is switched off.

SOFTWARE OF THE PRESENT EMBODIMENT

Figure 4:
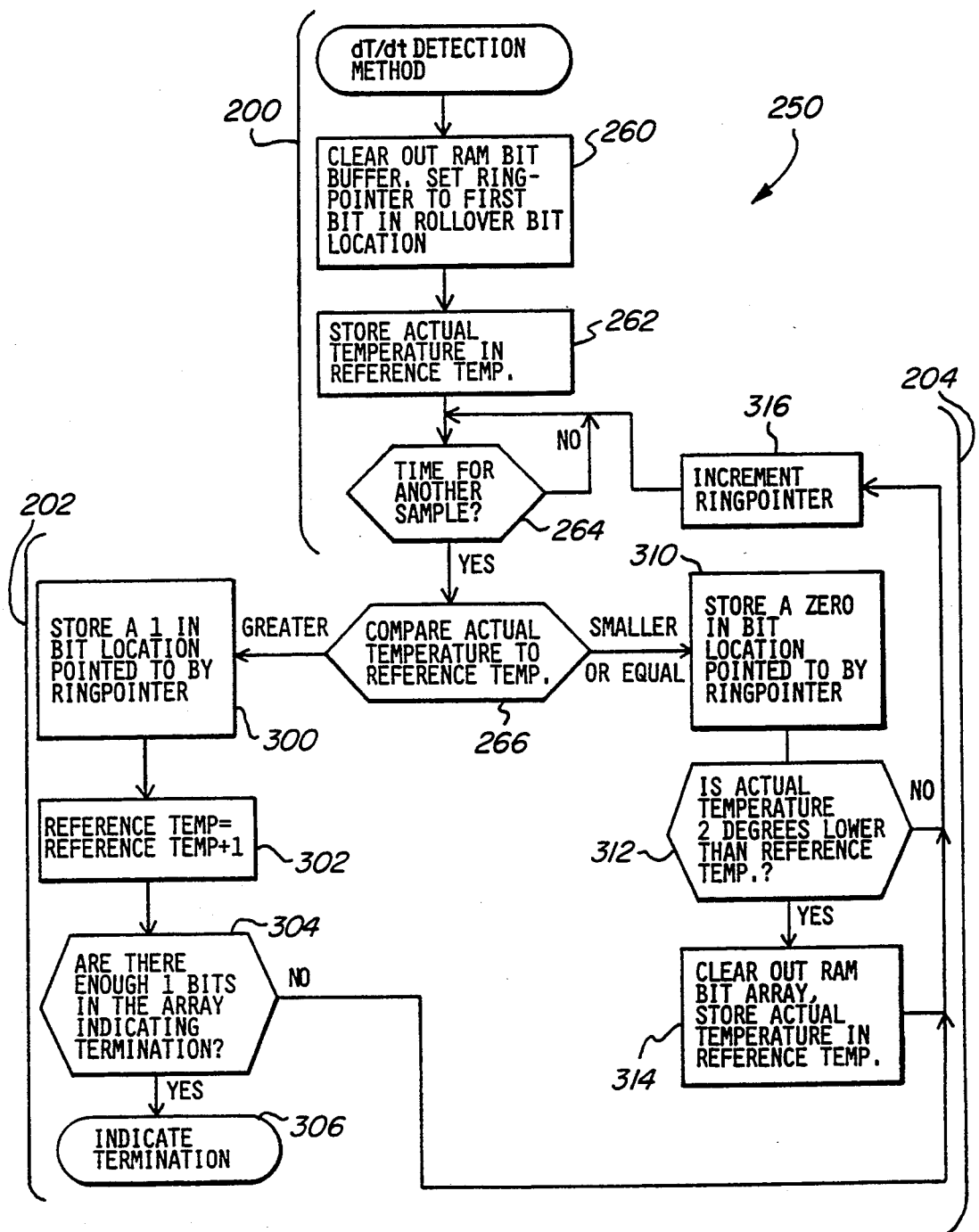
FIG. 4 illustrates a flow chart of one embodiment of the present invention which illustrates the logic applied by the computer 38a of FIG. 3.

FIG. 4 illustrates the software of the computer 38a which controls the hardware illustrated in FIG. 3. The FIG. 4 progression (a present embodiment of the dT/dt detection method 250) contains three sections: an initialization section 200, a comparative section 202, and a reduction section 204. The initialization section 200 sets up the computer to commence operation and determines the actual differential temperature 102 of the reference temperature store 104. The comparative section 202 determines when a suitable value of dT/dt has been reached and terminates charging by the charging device 24. The reduction section 204 reduces the value of the reference temperature store 104 when the actual temperature (as indicated at the output 102 of the A/D converter) drops over time. The only time that this drop is expected is during the decrementing initial portion 40b illustrated in FIG. 2.

When the dT/dt detection method 250 is initially started, the initialization section, which includes four steps which are numbered 260, 262, 264 and 266, is entered. A "clear out RAM bit buffer, and set ring pointer to first bit in rollover bit location" step 260 performs the two functions outlined in the name of the step, and as such initializes the computer to operate the dT/dt method 250. A "store actual temperature in reference temperature store" step 262 takes the initial temperature reading of the output 102 of the A/D converter 100 (FIG. 3) and stores it in the reference temperature store 104. A "time for another sample?" step 264 acts as a timer to determine when sufficient time has passed to perform the succeeding sampling event (the action of this step is controllable by the human operator). A "compare actual temperature to reference temperature store" step 266 compares the temperature of the output 102 of the A/D converter 100 with the value of the reference temperature store 104 to determine which is larger. If the actual temperature is higher, then the dT/dt detection method 250 will enter the comparative section 202. If the reference temperature store 104 value is equal or larger then the reduction section 204 will be entered.

The comparative section 202 comprises four steps which are numbered 300, 302, 304 and 306. A "store a 1 in temperature counter pointed to by ring pointer" step 300 stores a value of 1 in the bit location (120–125) of the temperature counter 110 for that specific sampling event. A "reference temperature=reference temperature+1" step 302 increments the value of the reference temperature 104 by 1 and adds the newest value to the right-most bit location (or if there are empty bit locations, the left most empty bit location) of the temperature counter; moves each value in the temperature counter one bit position to the left (or if there are empty bit locations, maintains the position of all existing bits); and deletes the left most value if there are no empty bit locations. An "are there enough 1 bits in the temperature counter array?" step 304 causes the summer 140 to count the number of "1's" values contained in the temperature counter 110 and compares the total to a predetermined limit (which is set by the user and corresponds to the dT/dt limit). If the predetermined limit is greater, then the dT/dt detection method 250 will input a zero in the appropriate bit position of the ring counter 110, and then index the ring counter to the next bit location. If, on the other hand, the total number of "1's" equal the predetermined limit, then the dT/dt detection method 250 will enter an "indicate termination" step 306, at which point the application of the charging device 24 will be terminated and some indicator to the user (a light, bell, etc.—not shown) will be activated. At this point, the dt/dt detection method has performed its function.

The reduction section 204 consists of four steps which are numbered 310, 312, 314 and 316. A "store a zero in bit location of temperature counter pointed to by ring counter" step 310 will store a zero in the one bit location 120–125 of the temperature counter 110 designated by the ring pointer 126. Specifically, it will add the newest value to the right-most bit location or, if there are empty bit locations, the left most empty bit location of the temperature counter. It will also move each value originally contained in the temperature counter one to the left or, if there are empty bit locations, maintain the position of all existing bits. It will also delete the left most value if there are no empty bit locations.

An "is actual temperature 2 degrees lower than reference temperature store?" step 312 compares the actual temperature contained in the output 102 of the A/D converter 100 with the value which is stored in the reference temperature store 104. The only time during charging when the question in step 312 should be answered in the affirmative is when the temperature is dropping as may occur in the decrementing initial portion 40b. An arbitrarily high level of two degrees can be selected at step 302 to override the possibility of random electronic noise which might provide an indication of one degree lower than actual in a system that uses single digit readings (a decrease from 8.01 to 7.99, for example). The possibility that random noise would register a reading that is two degrees lower than actual is substantially less than the possibility of a one degree error. Therefore, if the temperature indicated in the comparative step 266 indicates a drop of two degrees, the user can be certain that the temperature drop is real.

A "clear out RAM bit array, store actual temperature in reference temperature store" 314 accomplishes the processes of placing the most recent (lower) value of the output 102 of the A/D converter 100 (the actual temperature) into the reference temperature store 104 and clearing out any data previously stored in the temperature counter 110. This step follows the logic that a decrease in cell pack 12 temperature shall be accompanied by a continuation of charging by the charging device 24, and also that the dT/dt detection method 250 should continue with the lowest temperature of the reference temperature store 104 corresponding to the lowest actual temperature reached. In addition, step 314 has the effect of lowering the value contained in the reference temperature store 104 such that termination of the dT/dt detection method 250 (reaching step 306) occurs more reliably and readily. The final step in the reduction section 204 is an "increment ring pointer"

step 316 (which can also be accessed with a negative response from the "are there enough 1 bits in the array indicating termination?" step 304 of the comparative section 202) The "increment ring pointer" step 316 sets the ring pointer 126 to the left most bit location 120 of the temperature counter 110, such that the dT/dt detection method 250 will be in the correct position to start over again.

The present invention embodiment of the dT/dt detection method provides a method which will reliably indicate a desired dT/dt ratio (or above) but with a significantly reduced amount of occupied RAM than the prior art dT/dt methods. For illustration, reference is made to the previous example that monitored a 6 degree temperature rise over a 15 minute period, and in which temperatures are sampled every 10 seconds. The FIGS. 3 and 4 embodiment requires only 12 bytes of RAM storage (1 bit for each sampling event), which is less than one seventh of the 90 bits required for the above described prior art embodiment. The above flow charts, steps, figures and values of the present invention are to be considered as illustrative and not limiting in scope.

We claim:

1. A method for detecting when a cell pack reaches a full charge comprising the steps of:

sensing an actual temperature of the cell pack;

storing an initial actual temperature of the cell pack as a reference temperature;

determining, during subsequent sampling events, when said actual temperature exceeds said reference temperature;

storing in a rollover memory a first value for each sample event when said actual temperature exceeds the reference temperature, and a second value when the actual temperature does not exceed said reference temperature;

summing the occurrences of said first values for a series of consecutive sampling events to derive a total and determining from said total that the cell pack has reached a full charge.

2. The method as described in claim 1, further comprising the step of:

incrementing said reference temperature value by a known value for each sample event that said actual temperature does exceed said reference temperature.

3. The method as described in claim 1, wherein said first value is one and said second value is zero.

4. The method as described in claim 1, wherein said determining step further comprises the step of:

comparing said total to a predetermined limit.

* * * * *